United States Patent
Lee et al.

(10) Patent No.: US 10,973,941 B2
(45) Date of Patent: Apr. 13, 2021

(54) ECO-FRIENDLY SYSTEM FOR PREVENTING TOILET MALODOR

(71) Applicant: Purdue Research Foundation, West Lafayette, IN (US)

(72) Inventors: Kuan-Ting Lee, Lafayette, IN (US); Yudi Wen, Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 322 days.

(21) Appl. No.: 15/936,580

(22) Filed: Mar. 27, 2018

(65) Prior Publication Data

US 2018/0272021 A1    Sep. 27, 2018

Related U.S. Application Data

(60) Provisional application No. 62/476,904, filed on Mar. 27, 2017.

(51) Int. Cl.
| | |
|---|---|
| *A61L 9/013* | (2006.01) |
| *A61L 11/00* | (2006.01) |
| *A61L 9/05* | (2006.01) |
| *C11D 3/382* | (2006.01) |
| *C11D 3/48* | (2006.01) |
| *E03D 9/00* | (2006.01) |

(52) U.S. Cl.
CPC .......... *A61L 9/013* (2013.01); *A61L 9/05* (2013.01); *A61L 11/00* (2013.01); *C11D 3/382* (2013.01); *C11D 3/48* (2013.01); *E03D 9/007* (2013.01)

(58) Field of Classification Search
CPC . A61L 9/013; A61L 9/05; A61L 11/00; C11D 3/48; C11D 3/382
See application file for complete search history.

(56) References Cited

U.S. PATENT DOCUMENTS 7,947,311 B2 *   5/2011   Porter ................... A01N 65/24
                                                                                424/725

OTHER PUBLICATIONS

Anonymous, Methyl Soyate Is the Key Ingredient in Eco-Friendly Products, May 2006 downloaded online at: https://soynewuses.org/case-study/methyl-soyate-is-the-key-ingredient/(Year: 2006).*
United Soybean Board, "Soy Product Handbook", 2015.

* cited by examiner

*Primary Examiner* — Robert A Wax
*Assistant Examiner* — Nabila G Ebrahim
(74) *Attorney, Agent, or Firm* — Purdue Research Foundation; Liang Zeng Yan

(57) ABSTRACT

The present invention provides a soybean based non-toxic, non-hazardous, user and environmentally friendly odor trapping composition matter as a toilet spray. This product not only limits the undesired smell from defecation and releases a desirable smell, but also has potential antimicrobial properties to sanitize the toilet bowl.

14 Claims, No Drawings

ECO-FRIENDLY SYSTEM FOR PREVENTING TOILET MALODOR

CROSS-REFERENCE TO RELATED APPLICATIONS

The present U.S. patent application is related to and claims the priority benefit of U.S. Provisional Patent Application Ser. No. 62/476,904, filed Mar. 27, 2017, the contents of which are hereby incorporated by reference in their entirety into the present disclosure.

TECHNICAL FIELD

The present application relates generally to a composition matter for preventing toilet malodor, particularly to a composition manufactured from the products of soybean.

BACKGROUND

This section introduces aspects that may help facilitate a better understanding of the disclosure. Accordingly, these statements are to be read in this light and are not to be understood as admissions about what is or is not prior art.

The present invention relates to a composition matter for preventing toilet malodor. The general concept of a toilet deodorant is known. An example of such a product is sold under the trademark Poo-pourri. A primary ingredient of this existing product is polypropylene glycol and a description of such a product can be found in Carter, WO 2014113706 A1.

SUMMARY

The present invention provides a soybean based non-toxic, non-hazardous, user and environmentally friendly odor trapping composition as a toilet spray. This product not only limits the undesired smell from defecation and release a desirable smell, but also has potential antimicrobial properties to sanitize the toilet bowl.

The disclosed toilet deodorant may function as a substitute for an aerosol air-freshener. There are multiple places the disclosed toilet deodorant can be applied when the consumer wants to eliminate odor from defecation. It can be either used individually such as at home or in a to-go situation, or it can be used as a continuous supplement in the public bathroom at school, building halls, hotels, airplane, and trains, etc. to keep the air fresh in public places.

This product is especially useful in restrooms where ventilation is a problem, or where toilet pipe reflux happens that causes a stinky smell. Also, when camping, this product can be used in the portable toilet to reduce odors without using potentially toxic or hazardous chemical compounds.

Corresponding reference characters indicate corresponding parts throughout the several views. Although the exemplification set out herein illustrates an embodiment of the invention, in one form, the embodiment disclosed below is not intended to be exhaustive or to be construed as limiting the scope of the invention to the precise form disclosed.

These and other features, aspects and advantages of the present invention will become better understood with reference to the following detailed description and claims.

DETAILED DESCRIPTION OF THE INVENTION

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

As used herein, the following terms and phrases shall have the meanings set forth below. Unless defined otherwise, all technical and scientific terms used herein have the same meaning as commonly understood to one of ordinary skill in the art.

In the present disclosure the term "about" can allow for a degree of variability in a value or range, for example, within 20%, within 10%, within 5%, or within 1% of a stated value or of a stated limit of a range. In the present disclosure the term "substantially" can allow for a degree of variability in a value or range, for example, within 80%, within 90%, within 95%, or within 99% of a stated value or of a stated limit of a range.

A derivative is something that is based on another source or a substance that is derived chemically from a specified material. For example, a soybean oil derivative is something prepared using soybean oil as the main starting material (Scheme 1); and a crack is a highly addictive cocaine derivative.

The present invention provides a soybean based non-toxic, non-hazardous, user and environmentally friendly odor trapping composition as a toilet spray. This product will not only limit the undesired smell from defecation and release a desirable smell, but also has potential antimicrobial properties to sanitize the toilet bowl.

The disclosed toilet deodorant can function as a substitute for an aerosol air-freshener. There are multiple places the disclosed toilet deodorant can be applied when the consumer wants to eliminate odor from defecation. It can be either used individually such as at home or in a to-go situation, or it can be used as a continuous supplement in the public bathroom at school, building halls, hotels, airplane, and trains, etc. to keep the air fresh in public places.

This product is especially useful in restrooms where ventilation is a problem, or where toilet pipe reflux happens that causes a stinky smell. Also, when camping, this product can be used in the portable toilet to reduce odors without using potentially toxic or hazardous chemical compounds.

The disclosed toilet deodorant mainly contains derivatives from soybean. The product disclosed herein is an all-natural soybean based odor trapping spray that is sprayed on the upper water surface in a toilet bowl before going to the toilet. The general idea of the disclosed deodorant is to make a barrier between the waste and air using soybean oil as large molecular weight product that can serve as a barrier.

Scheme 1. Preparation of Methyl Soyate, a Soybean Oil Derivative

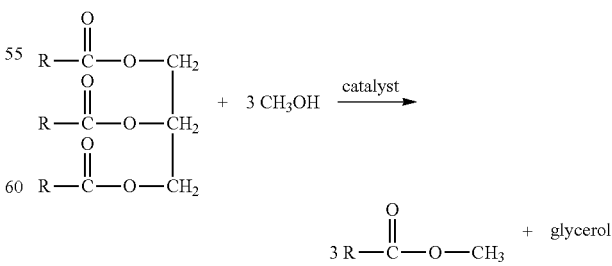

A homogenizer and soy lecithin (emulsifier) are used to generate an emulsion of the two immiscible liquids (soybean oil and water) which is meta-stable. The deodorant may be manufactured using all natural ingredients and effectively traps odors and keeps the toilet bowl sanitized after defecation.

The disclosed product is a good substitution for an aerosol air-freshener, which is a common odor-reducing spray used in bathrooms. From a press released by *Grand View Research*, in the global aerosol air-freshener market, the demand for aerosol air-freshener was 15.28 billion units in 2015. Many of the aerosol air-fresheners in today's market contains chemical products that pose a risk to our respiratory system after a long-term inhalation or irritation after contacting the product with skin. Aerosol air-fresheners only mask the smell and do not eliminate the smell.

In contrast, the product disclosed herein mainly contains soybean oil and soybean derivative product, which are all natural and safe to use. It is non-toxic, biodegradable, user friendly, non-hazardous, environmental friendly, bio-based product. The disclosed product traps the smell instead of masking the smell. The disclosed deodorant can also include essential oils or other suitable substance free of toxic components to provide it with an agreeable fragrance.

In some illustrative embodiments, the present invention relates to a toilet deodorant composition comprising soybean oil or its derivative, soy lecithin, and water.

In some illustrative embodiments, the present invention relates to a toilet deodorant composition, wherein the toilet deodorant composition further comprises an essential fragrant oil.

In some illustrative embodiments, the present invention relates to a toilet deodorant composition, wherein the toilet deodorant composition further comprising an essential fragrant oil, which is selected from the group consisting of Lavender essential oil, *Eucalyptus* Essential Oil, Orange Essential Oil, Bergamot Essential Oil, Cinnamon Essential Oil, Rose Otto Essential Oil, Ylang Ylang Essential Oil, Jasmine Absolute, Patchouli Essential Oil.

In some illustrative embodiments, the present invention relates to a toilet deodorant composition, wherein the composition is homogenized to a stable suspension.

In some illustrative embodiments, the present invention relates to a toilet deodorant composition, wherein said soybean oil derivative is methyl soyate.

In some illustrative embodiments, the present invention relates to a toilet deodorant composition, wherein said soybean oil accounts for about 10% to about 50% of said composition.

In some illustrative embodiments, the present invention relates to a toilet deodorant composition, wherein said soybean oil accounts for about 15% to about 35% of said composition.

In some illustrative embodiments, the present invention relates to a toilet deodorant composition, wherein said soybean oil accounts for about 15% to about 25% of said composition.

In some illustrative embodiments, the present invention relates to a toilet deodorant composition, wherein said soy lecithin accounts for about 1% to about 10% of said composition.

In some illustrative embodiments, the present invention relates to a toilet deodorant composition, wherein said soy lecithin accounts for about 1% to about 5% of said composition.

In some illustrative embodiments, the present invention relates to a product adapted to be applied to a toilet bowl before use of the toilet comprising soybean oil or its derivatives, soy lecithin, and water.

In some illustrative embodiments, the present invention relates to a product adapted to be applied to a toilet bowl before use of the toilet, wherein the product further comprising an essential fragrant oil.

In some illustrative embodiments, the present invention relates to a product adapted to be applied to a toilet bowl before use of the toilet, wherein soybean oil, soy lecithin, water and the essential fragrant oil are homogenized to a stable suspension.

In some illustrative embodiments, the present invention relates to a product adapted to be applied to a toilet bowl before use of the toilet, wherein said essential fragrant oil is selected from the group consisting of Lavender essential oil, *Eucalyptus* Essential Oil, Orange Essential Oil, Bergamot Essential Oil, Cinnamon Essential Oil, Rose Otto Essential Oil, Ylang Ylang Essential Oil, Jasmine Absolute, Patchouli Essential Oil.

In some illustrative embodiments, the present invention relates to a product adapted to be applied to a toilet bowl before use of the toilet, wherein said soybean oil derivative is methyl soyate.

In some illustrative embodiments, the present invention relates to a product adapted to be applied to a toilet bowl before use of the toilet, wherein said soybean oil accounts for about 10% to about 50% of said composition.

In some illustrative embodiments, the present invention relates to a product adapted to be applied to a toilet bowl before use of the toilet, wherein said soybean oil accounts for about 15% to about 35% of said composition.

In some illustrative embodiments, the present invention relates to a product adapted to be applied to a toilet bowl before use of the toilet, wherein said soybean oil accounts for about 15% to about 25% of said composition.

In some illustrative embodiments, the present invention relates to a product adapted to be applied to a toilet bowl before use of the toilet, wherein said soy lecithin accounts for about 1% to about 10% of said composition.

In some illustrative embodiments, the present invention relates to a product adapted to be applied to a toilet bowl before use of the toilet, wherein said soy lecithin accounts for about 1% to about 5% of said composition.

In some preferred embodiments, the product contains the components listed below. The list below represents the material used to make the exemplary embodiment and equipment utilized in a testing manufacture process.

Raw Material List

Soybean Oil 19%

Soy lecithin 3%

Water 76.5%

Lavender Essential Oil 1.5%

Bottle: spray bottle

Packaging: foam board and poster card board

Manufacturing Equipment: Homogenizer, Water Purifier

For the essential oil, the illustrated example was produced with 100% Lavender essential oil from Pure & Natural Therapeutic Grade®. Other essential oils and fragrances may be used in alternative embodiments.

For the bottle, the illustrated example was produced using an aluminum spray bottle mist obtained from Alibaba.com.

For the ingredients, the illustrated example included 19% soybean oil and 3% soy Lecithin, which contains 35% soybean oil.

Soybean oil contains glycerin, lipids and other non-polar molecules that serve as a surface barrier agent that separates water in the toilet bowl and air by hydrophobic effect. The disclosed product, which is primarily soybean oil, has potential antimicrobial properties that can help keep the toilet bowl sanitized. This potential anti-bacterial property is provided by the methyl soyate. The disclosed product is non-hazardous, user friendly and safe.

The disclosed product is a light yellow colored liquid. After the product is sprayed onto the water surface, it creates a pale white cloudy layer on top of the water. The packaging used with the product can be used to inform the consumer of its purpose and manner of use. For example, it may take the form of a three dimensional mini toilet seat where the spray bottle sits on top of the toilet seat. This visual design creates a clearer purpose of what our product is about by simply looking at the appearance of the product without reading the description on the bottle.

The exemplary embodiment disclosed herein is a soybean based non-toxic, nonhazardous, user and environmentally friendly odor trapping before-toilet spray which creates a barrier between the toilet water and air. It can be used as a substitute for aerosol air-fresheners.

A flowchart representing the process of manufacturing a toilet deodorant as disclosed herein is presented here:
  Obtain Raw Materials:
    19 Vol. % Soybean Oil
    3 Vol. % Soy lecithin (liquid)
    76.5 Vol. % Water
    1.5 Vol. % Essential Oils
  Dissolve Soy Lecithin in Water:
    Heat to 70-80° C. and Stir to dissolve overnight.
  Mixing ingredient:
    Soybean oil and essential oil were added into the dissolved soy lecithin solution and emulsified with homogenizer (KIKA ULTRA-TURRAX® T 50 basic). The speed was gradually increased to 10,000 rpm (revolutions per minute), emulsify for 5 minutes.
    Homogenizer Requirement: The higher homogenization speed generates the smaller the particle size, and more stable the emulsion system.
    Analysis of droplet size (Master Sizer): To ensure the appearance consistency and the stability of the product.
  Fill Bottles (2 Oz): A fine mist spray bottle is required for even distribution of the product.
  Package Soybean oil is hydrophobic and hence is immiscible in water. Soybean oil also has a lower density than water, thus when mixing with water, it will float on top of the water. The emulsion system of soybean oil in water can serve as an effective barrier to trap odor generated by defecation because the floating soybean oil will reduce the contact between air and water, and the emulsified soybean oil droplets can adhere around the hydrophobic feces to reduce odor emission.

Creating an oil-in-water emulsion makes the product less viscous, and greasy and provides it with more consistency compared to soybean oil alone. By adding water as the carrier of the soybean oil, the resulting product has a viscosity that allows it be sprayed from a mist bottle.

Soy lecithin, another soybean derivative, is a food grade surfactant that is used to stabilize the oil-in-water emulsion system. This surfactant has an amphiphilic property that its hydrophobic side can interact with oil droplets, and the hydrophilic end can interact with water, creating an interface between two immiscible substances to prevent coagulation of oil droplets when external shear force is applied to the emulsion system. The use of surfactant stabilizes the emulsion and makes the emulsion more uniform.

Moreover, because the oil-in-water emulsion has oil droplets which are surrounded by surfactant, the outer interface of the droplets are thus hydrophilic. This feature reduces the greasiness of the product and makes the spray easier to be flushed by water after application.

Based on volume percentage, the exemplary product is composed of about 19% soybean oil, about 76% water, about 3% of soy lecithin, and about 1.5% essential oil. Overall, about 99% of the product is composed of soy components and water.

The quality of the product is dependent, in part, on control of the droplet size and the stabilization of the emulsion system. To control these parameters, a high-speed homogenizer was used. The higher speed of the homogenization process, the smaller the droplet size, and a more stable emulsion system can be produced. The particle size of each product was determined by the Master Sizer, which was used as a quality control point for the exemplary product. Since soy lecithin has relatively low solubility, to dissolve the soy lecithin in water, it may be desirable to use water at an elevated temperature of 70-80° C. and for an extended time for better dissolution.

For the exemplary embodiment, filling bottles and packaging were both a hand-made process. For larger scale production, machines will be used to fill the bottles with product, cap and seal the filled bottle. For packaging, a box folding machine would be used for larger scale production and/or customized packaging equipment employing existing technology. The disclosed embodiment highly feasible to be manufactured with existing facilities and technologies.

The homogenizer used for production of the exemplary embodiment was a KIKA ULTRA-TURRAX® T 50 basic, which can provide a 10,000 rpm (revolutions per minute) speed for homogenization. For the quality test of the exemplary embodiment, a Master Sizer equipped to test the particle size was employed.

The exemplary product contains water, soybean oil, natural essential oil, and soy lecithin. All of these ingredients are from natural sources and are non-hazardous when they come into contact with skin. A fragrance, such as an essential oil from lavender, lemon or tea tree may also be included in the disclosed deodorant.

The disclosed product can be packaged in a small convenient spray bottle that makes it convenient to carry and suitable in many situations. A small spray bottle of the disclosed product can be carried in a bag or purse so that it can be used when traveling outside the house as well as at home. For example, it could be used at a friend's house, public space or even airplane (limited to 3.4 ounces).The non-toxic and non-hazardous property make it more feasible to carry and use in all kinds of circumstance.

Materials acquired during the manufacture of a proof of concept embodiment are listed below. Not all of the listed materials are necessarily ingredients in the final product which are described elsewhere.
  Sources of materials:
  Sigma-Aldrich:
  Poly(propylene glycol) 202339-250G
    ASIN: 202339
  Source: Amazon:
  NOW Solutions Glycerine Vegetable, 16-Fluid Ounces
    ASIN: B0019LWU2K
  Food Coloring Liqua-Gel—12 Color Variety Kit in 0.75 fl. oz. (20 ml) Bottles
    ASIN: B01DWEZB5E
  12, Amber, 2 oz Glass Bottles, with Black Fine Mist Sprayers ASIN: B00V75IIU6
Pure Liquid Soy Lecithin (Food Grade) ASIN: B00PD7FPVE
Radha Beauty Lavender Essential Oil 4 Oz—100% Pure & Natural Therapeutic Grade
ASIN: B00QQOERJE
Radha Beauty Lemon Essential Oil 4 Oz
ASIN:B01KK8GTAG
Radha Beauty *Eucalyptus* Essential Oil—Big 4 Oz
ASIN:B00Y1CDNXO
Radha Beauty Rosehip Oil 4 oz—100% Pure Cold Pressed Certified Organic
ASIN: B00LNOV8JO
2 oz Plastic Spray Bottles with Fine Mist Sprayers
ASIN: B01LZ29CKI Those skilled in the art will recognize that numerous modifications can be made to the specific implementations described above. The implementations should not be limited to the particular limitations described. Other implementations may be possible.

While the inventions have been illustrated and described in detail in the drawings and foregoing description, the same is to be considered as illustrative and not restrictive in character, it being understood that only certain embodiments have been shown and described and that all changes and modifications that come within the spirit of the invention are desired to be protected. It is intended that the scope of the present methods and apparatuses be defined by the following claims. However, it must be understood that this disclosure may be practiced otherwise than is specifically explained and illustrated without departing from its spirit or scope. It should be understood by those skilled in the art that various alternatives to the embodiments described herein may be employed in practicing the claims without departing from the spirit and scope as defined in the following claims.

The invention claimed is:

1. A toilet deodorant composition consisting of a mixture of soybean oil or its derivative, soy lecithin, a fragrance for covering unpleasant odor of the toilet, and water, wherein water accounts for more than 50% of the mixture and said mixture is emulsified to a stable suspension using a homogenizer at a speed of about 10,000 rpm or higher.

2. The toilet deodorant composition according to claim 1 wherein said fragrance is selected from the group consisting of lavender essential oil, Eucalyptus Essential Oil, Orange Essential Oil, Bergamot Essential Oil, Cinnamon Essential Oil, Rose Otto Essential Oil, Ylang Ylang Essential Oil, Jasmine Absolute, Patchouli Essential Oil.

3. The toilet deodorant composition according to claim 1, wherein said soybean oil derivative is methyl soyate.

4. The toilet deodorant composition according to claim 1, wherein said soybean oil accounts for about 15% to about 35% of said composition.

5. The toilet deodorant composition according to claim 1, wherein said soybean oil accounts for about 15% to about 25% of said composition.

6. The toilet deodorant composition according to claim 1, wherein said soy lecithin accounts for about 1% to about 10% of said composition.

7. The toilet deodorant composition according to claim 1, wherein said soy lecithin accounts for about 1% to about 5% of said composition.

8. A product adapted to be applied to a toilet bowl before use of the toilet consisting of a mixture of soybean oil or its derivatives, soy lecithin, a fragrance for covering unpleasant odor of the toilet, and water, wherein water accounts for more than 50% of the mixture and said mixture is emulsified to a stable suspension using a homogenizer at a speed of about 10,000 rpm or higher.

9. The product according to claim 8 wherein said fragrance is selected from the group consisting of lavender essential oil, Eucalyptus Essential Oil, Orange Essential Oil, Bergamot Essential Oil, Cinnamon Essential Oil, Rose Otto Essential Oil, Ylang Ylang Essential Oil, Jasmine Absolute, Patchouli Essential Oil.

10. The toilet deodorant composition according to claim 8, wherein said soybean oil derivative is methyl soyate.

11. The product according to claim 8, wherein said soybean oil accounts for about 15% to about 35% of said composition.

12. The product according to claim 8, wherein said soybean oil accounts for about 15% to about 25% of said composition.

13. The product according to claim 8, wherein said soy lecithin accounts for about 1% to about 10% of said composition.

14. The product according to claim 8, wherein said soy lecithin accounts for about 1% to about 5% of said composition.

* * * * *